(12) United States Patent
Jobdevairakkam et al.

(10) Patent No.: US 7,585,978 B2
(45) Date of Patent: Sep. 8, 2009

(54) PROCESSES OF MANUFACTURING SUBSTITUTED-1,4-DIHYDROPYRIDINES, IMPROVED AQUEOUS SOLUTIONS THEREOF, AND PROCESSES OF MANUFACTURING THE SOLUTIONS

(75) Inventors: Christopher N. Jobdevairakkam, Plainsboro, NJ (US); Jayaraman Kannappan, Piscataway, NJ (US)

(73) Assignee: Navinta LLC, Ewing, NJ (US)

( * ) Notice: Subject to any disclaimer, the term of this patent is extended or adjusted under 35 U.S.C. 154(b) by 0 days.

(21) Appl. No.: 11/605,112

(22) Filed: Nov. 28, 2006

(65) Prior Publication Data
US 2008/0125595 A1    May 29, 2008

(51) Int. Cl.
*C07D 213/803* (2006.01)
*C07D 401/00* (2006.01)
*C07D 211/68* (2006.01)

(52) U.S. Cl. ............... 546/321; 546/194; 546/276.4
(58) Field of Classification Search ............... 546/194, 546/276.4, 321
See application file for complete search history.

(56) References Cited

U.S. PATENT DOCUMENTS

| | | | | |
|---|---|---|---|---|
| 3,985,758 A | * | 10/1976 | Murakami et al. | 546/321 |
| 4,769,465 A | | 9/1988 | Antoncic et al. | |
| 5,164,405 A | * | 11/1992 | McFarlane et al. | 514/354 |

FOREIGN PATENT DOCUMENTS

| | | | | |
|---|---|---|---|---|
| EP | 0445987 A2 | * | 1/1991 | |
| ES | 499727 | * | 5/1982 | |
| JP | 111-3234 | * | 7/1999 | |
| JP | 11193234 | * | 7/1999 | |

OTHER PUBLICATIONS

Noyola et al. Revista de la Sociedad Quimica de Mexico (2003), 47(1), 34-37.*

* cited by examiner

*Primary Examiner*—D. Margaret Seaman
*Assistant Examiner*—Nizal S Chandrakumar
(74) *Attorney, Agent, or Firm*—St. Onge Steward Johnston & Reens LLC (57) ABSTRACT

A process of preparing a stable parenteral solution of a 1,4-dihydropyridine salt, such as nicardipine hydrochloride, in an acidic aqueous medium. The presence of L-arginine in the solution enhances the solubility of the salt, which is poorly soluble in water.

An aqueous, injectable isotonic solution at pH about 3.5-3.6 consists essentially of nicardipine hydrochloride, L-arginine, and a sugar alcohol.

An improved single pot manufacturing process for obtaining unsymmetrical 1,4-dihydropyridines by using more than one mole equivalent of aldehyde with respect to the other reactants (amino crotonate and acetoacetate ester). The reaction can be conducted in a solvent present at 20 times the amount of any one component.

A process for changing one polymorph of nicardipine hydrochloride (Form A) into another (Form B), and a separate process for the reverse (Form B into Form A).

11 Claims, 3 Drawing Sheets

Figure-1 X-Ray powder diffractogram of nicardipine hydrochloride Form B prepared by Example-4

Figure-2 X-Ray powder diffractogram of Nicardipine hydrochloride melting at about 135°C prepared by Example-3.

FIGURE-3 Change in pH of Nicardipine parenteral solution against added volume of 0.05 M TRIS ;
- - - -   Nicardipine hydrochloride by Example-11
———   Nicardipine Hydrochloride (Cardene)

FIGURE-4 Buffer Capacity of Nicardipine hydrochloride parenteral formulation; plot of difference in pH of Nicardipine hydrochloride solution ( Δ pH) against the initial pH of added dextrose solution

PROCESSES OF MANUFACTURING SUBSTITUTED-1,4-DIHYDROPYRIDINES, IMPROVED AQUEOUS SOLUTIONS THEREOF, AND PROCESSES OF MANUFACTURING THE SOLUTIONS

BACKGROUND OF INVENTION

1,4-Dihydropyridines are known to treat hypertension and are classified mainly as calcium channel blockers. First synthetic process for 1,4-dihydropyridines was reported by Arthur Hantzsch (Justus Liebigs Ann. Chem., 1882, 215, 1) In general commercial manufacturing of 1,4-dihydropyridines involves reaction of an aromatic aldehyde, an amine/ammonia and β-keto ester derivatives.

Several pharmaceutically acceptable 1,4-dihydropyridine-3,4-dicarboxylic acid derivatives are known in the literature such as nicardipine, felodipine, nifedipine, nimodipine, nisoldipine, etc., Substituents at 3 and 5 position of 1,4-dihydropyridines categorizes these molecules either symmetrical or unsymmetrical. Symmetrical 1,4-dihydropyridines are relatively easy to synthesis with much purity and yield.

Four different synthetic approaches are known in the art to synthesis unsymmetric 1,4-dihydropyridines The first procedure involves preparation of the benzylidene derivative from the aromatic aldehyde and the amino crotonate. The benzylidene derivative is further reacted with β-keto ester to yield the 1,4-dihydropyridines. (Scheme-1). In Example 7 of German patent 2407115 (U.S. Pat. No. 3,985,758) there is described a for obtaining nicardipine in an overall yield of approximately 12% by reacting the intermediate chloroethyl methyl 2,6-dimethyl-4-(m-nitrophenyl)-1,4-dihydropyridine-3,5-dicarboxylate with N-methyl benzyl amine.

The second procedure (Scheme-2) involves preparation of benzylidene derivatives from the aromatic aldehyde and the β-keto ester; in some reports a catalyst was used at this stage, and then the benzylidene derivative is reacted with amino crotonate to produce the 1,4-dihydropyridines. The yield achieved when using this procedure has been problematic. Specifically, the generally poor overall yield of nicardipine using this procedure is due to a lack of purity in the intermediates, such as 2-(N-benzyl-N-methylamino)-ethyl acetoacetate, which is obtained at a very poor yield of 10.5% by reacting 2-(N-benzyl-N-methylamino)-ethanol with ethyl acetoacetate in an anhydrous medium (M. Iwanami et al., Chem. Pharm. Bull. 27(6), 1426-1440 (1979)). Examples in the art using this procedure are given for 1,4-dihydropyridine derivatives in U.S. Pat. No. 3,932,645 and U.S. Pat. No. 6,689,799, for Amlodipine in U.S. Pat. No. 6,784,297, and for nicardipine hydrochloride in JP 8217749.

U.S. Pat. No. 3,932,645 reports a process of making 1,4dihydropyridines by condensing an aldehyde with an acetoacetate to yield a benzylidene intermediate, and further reaction with amino crotonates or acetoacetate and amine/ammonia. As referred to in U.S. Pat. No. 6,858,747, when acid is used as a catalyst in the preparation of the benzylidene derivative, a mixture of aldol by-products are observed; this is also reported in U.S. Pat. No. 5,310,917, and similar examples are reported in U.S. Pat. No. 5,977,369 and U.S. Pat. No. 4,600,778. U.S. Pat. No. 6,649,767 discloses one pot, two stage reactions catalyzed by magnesium (II) base at the benzylidene stage and by an acid at the condensation stage.

The third procedure involves conversion of symmetric 1,4-dihydropyridine by selectively replacing one of the ester moieties by a desired substitution (Scheme-3). This approach also has a poor yield and a high level of impurities in downstream products. It is known that N-aryl- or N-alkyl-substituted dihydropyridine-3,5-dicarboxylates are easily hydrolyzed under the action of alkalis to the corresponding dihydropyridine-monocarboxylic acids (A. Sausins et al., Khim. Geterocikl. Soedin., 2, 272 (1978)). Contrary to the easy alkaline hydrolysis of N-aryl- and N-alkyl-substituted dihydropyridine-3,5-dicarboxylates, the N-unsubstituted dihydropyridine-3,5-dicarboxylates are not, or are only to a small extent, hydrolyzed to the corresponding monoesters of dicarboxylic acids (N. Eisner et al., Chem. Rev. 72, 1, 4 (1972) or B. Loev et al., J. Heterocyclic Chem. 12, 363 (1975); M. Iwanami et al., Chem. Pharm. Bull. 27(6), 1426-1440 (1979), and T. Shibanuma, Chem. Pharm. Bull., 28(9) 2809-2812 (1980), JP 03017059, U.S. Pat. No. 4,818,855.) U.S. Pat. No. 4,769,465 describes a process of preparing nicardipine hydrochloride in overall yield amounts to 46% with respect to the starting materials.

Scheme-3

Symmetrical 1,4-dihydropyridine

Unsymmetrical 1,4-dihydropyridine

The fourth procedure (Scheme-4) is the preparation of unsymmetric 1,4-dihydropyridines by a one pot synthesis using an aldehyde, β-ketoester, and aminocrotonate or mixture of acetoacetate and an amine/amine salt. Even though the synthetic methodologies used for symmetrical 1,4-dihydropyridines could be used to synthesize unsymmetrical 1,4-dihydropyridines, the same yield and purity are not met and so the processes are not commercially successful. In EP0445987 and JP55860/90, single pot preparation of nicardipine hydrochloride (160 g, yield 25.8% by mole ratio) has been reported.

Scheme-4

Aminocrotonate  Beta keto ester

Unsymmetrical 1,4-dihydropyridine

General drawbacks with the reported synthetic processes of 1,4-dihydropyridines are poor yield and low purity. Most of the single pot syntheses of unsymmetrical 1,4-dihydropyridines provide a maximum yield of about 20% by mol with respect to the β-ketoester. The low yield is especially true in the case of nicardipine hydrochloride, which is poorly soluble in water, hence making it difficult to remove the impurities which are very similar in chromatographic characteristics of nicardipine hydrochloride.

Most of the 1,4-Dihydropyridine hydrochloride salts (especially nicardipine hydrochloride and nifedipine hydrochloride) are very poorly soluble in water. Methods for enhancing the solubility to produce a stable aqueous solution of 1,4-dihydropyridines are known in the art. The solubility of nicardipine hydrochloride is typically enhanced through the use of organic acids, such as citric acid, acetic acid, and the like. However, the use of mineral acids, especially hydrochloric acid, reduces the solubility of nicardipine hydrochloride at a pH in the range of 3 to 4, likely by the common ion effect. Thus, preparing a stable, parenteral, aqueous solution of nicardipine hydrochloride is of keen pharmaceutical interest.

Preparation of aqueous solution of nicardipine hydrochloride in presence of a polyhydric alcohol such as sorbitol, mannitol, xylitol etc., in a pH range of about 2.5 to 5.5 has been disclosed by Katayasu et al. (JP 102991/84, EP 0162705, U.S. Pat. No. 4,880,823, and U.S. RE34618). The data reported in EP0162705 reveals that the nicardipine hydrochloride in aqueous solution so produced is unstable and about 30% to about 50% of the potency is lost during storage. Preparation of a nicardipine parenteral solution has been reported by Calum et al. (U.S. Pat. No. 5,164,405) using a pharmaceutically acceptable buffer at a pH of about 3 to 4.5; the buffers described include citrate, acetate, phosphate, and lactate in presence of polyhydric alcohols such as mannitol, sorbitol, dextrose, glucose, polyethylene glycol, and glycerol.

Parenteral solutions of nicardipine are reported with added buffers (JP2000072673 and JP2003137782), with added phosphoric acid (JP 20033104889), with added calcium or sodium gluconate as stabilizer (JP2001316266), and with the addition of 2-HP-beta-cyclodextrin for the manufacture of a powder for making an injectable (CN1326731). Japanese patent JP 11193234 discloses parenteral solutions of nicardipine hydrochloride in which an acid is present; such acids include hydrochloride acid, phosphoric acid, tartaric acid, lactic acid, citric acid, amino acetic acid, glutamic acid, and alanine. None of the examples in this JP publication are specific to the use L-arginine; nevertheless the claims recite arginine, aspartic acid, and cysteine as examples of amino acids that can be used as the acid. Also in this JP publication, the ratio of the added amino acid to the nicardipine hydrochloride is about 1 to 50 times by weight. At this concentration of nicardipine hydrochloride to amino acid (1:1 to 50:1), the solubility of nicardipine hydrochloride will be very poor at room temperature; it would require heating to at least about 50° to 60° C. to dissolve the nicardipine HCl and obtain a clear solution. Such heat-assisted dissolution leads to degradation of nicardipine, giving several impurities, some of which might be toxic. It also has been reported in JP 1193234 that the parenteral solution of nicardipine hydrochloride prepared by using amino acids is not stable, that a significant drop in the nicardipine content of the parental solution (up to about 9.7%) is observed after only 21 days. This relatively poor storage stability is possibly due to thermal degradation of nicardipine, a reaction catalyzed by the excess concentration of amino acids present. It should be apparent that the use of an organic acid buffer in an aqueous solution with the intent to enhance the solubility of nicardipine hydrochloride in water would have stability concerns because the organic acid would likely participate in catalytic hydrolysis of the ester groups present on the nicardipine molecule. The nicardipine parenteral injectables marketed as Cardene brand solutions generally have degradation impurities at a level of more than 0.5%. The hydrolytic degradation products of nicardipine are shown in Scheme-6 below:

Nicardipine hydrolytic degregation products

In general, the prior one pot, single step syntheses of 1,4-dihydropyridines unsymmetrically substituted at the 3 and 5 positions used an equimolar ratio of the aldehyde, aminocrotonate and the β-keto ester. The prior processes lead to a significant yield of the symmetrical 3,5-substituted compounds, thereby reducing the yield and purity of the required 1,4-dihydropyridines. All the prior art manufacturing processes for nicardipine involve using one mole equivalent of aldehyde with regard to the β-keto ester and the amino crotonate. The overall yield with respect to β-keto ester is about 16 to 20% by mole.

SUMMARY OF INVENTION

One object on this invention is to provide an improved process of manufacturing nicardipine hydrochloride with good yield, and preferably also a purity greater than 99%. It is one aspect of this invention that the ratio of the aromatic aldehyde to the other reactants plays an important role in driving the reaction to completion and achieving better yield and purity. In this regard, this invention provides a single step one pot synthetic manufacturing process of preparing 1,4-dihydropyridines with good yield and purity, demonstrated by the preparation of nicardipine hydrochloride from 3-nitrobenzaldehyde, methyl aminocrotonate, and N-benzyl-N-methylaminoethyl acetoacetate (Scheme-5, according to this invention) Following the methods of this invention, an excellent yield of nicardipine hydrochloride is obtain by using more than one mole equivalent of the aldehyde with respect to the β-keto ester or aminocrotonate. The invention is also practiced by reacting essentially equimolar quantities of acetoacetic acid methyl ester, 3-aminocrotonic acid 2-(N-benzyl-N-methylamino)ethyl ester, and an amine base or salt with a supramolar amount of 3-nitrobenzaldehyde.

In another aspect of this invention is provided by conducting the reaction in a volume or weight of solvent at least 20 times the volume or weight, respectively, of any one of the components.

Another object of this invention is to provide a process of making a stable parenteral solution of nicardipine in an aqueous medium using an organic base, especially L-arginine. Use of L-arginine has been known in the art to be used for the preparation of parenteral compositions of poorly soluble drugs and pro-drugs. Also L-arginine is used as an excipient in a wide range of pharmaceutical application. In general, L-arginine is considered as organic base which has three pKa values at 2.18, 9.09, and 13.2. Buffer activity of a substance is effective in the range pKa±1 (K. A. Connors, *A text book of pharmaceutical analysis* (New York: John Wiley & Sons Inc, 1975), section 1.1; *The Merck Index*, 13$^{th}$ Ed. (Whitehouse Station, New Jersey: Merck & Co., Inc., 2001), entry #785.) Similarly, parenteral solutions of other 1,4-dihydropyridine salts which are poorly soluble in aqueous medium can be made by using L-arginine. Nevertheless, this invention provides both an improved process for making solutions of 1,4-dihydropyridine salts and improved aqueous solutions thereof, especially an injectable nicardipine solution with L-arginine in a pH regime where L-arginine is not a buffer, and without the prior art stability problems. This invention provides an aqueous injectable solution of nicardipine at a pH of from about 3.2 to about 7.6, more preferably from about 3.2 to about 4, and most preferably from about 3.5 to about 3.6, and preferably made isotonic through the addition of a sugar alcohol such as sorbitol.

Still further, this invention provides a process of preparing a nicardipine hydrochloride solution suitable for parenteral administration by dissolving nicardipine hydrochloride in an aqueous solution containing a combination of L-arginine and hydrochloric acid. Use of L-arginine facilitates the solubility of nicardipine hydrochloride in water at temperature at about 20 to 40° C., yielding a parenteral solution having better stability than those formulated with organic acid buffers.

This invention also provides a process of converting nicardipine hydrochloride Form B to nicardipine hydrochloride Form A, and a separate process of converting Form A to Form B.

DETAILED DESCRIPTION OF SPECIFIC EMBODIMENTS

The process of this invention provides a drastically improved process by employing more than one (1) mole equivalent of the aromatic aldehyde to at least one of the β-keto ester and the amino crotonate. The aldehyde is present in a molar ratio of at least about 1:1.2, more preferably about 1:1.5, and most preferably about 1:2 or more, with regard to one of the β-keto ester and the amino crotonate, and more preferably with respect to both. In the process of preparing unsymmetrical 1,4-dihydropyridines, the more probable by-products are the symmetrical 1,4-dihydropyridines. The issue of directing the selectivity of the reaction to form the desired unsymmetrical 1,4-dihydropyridines is not addressed in the prior art. The process of this invention is better than the prior art processes for producing the desired unsymmetrical 1,4-dihydropyridines selectively, providing better yield and purity. In more preferred embodiments, the solvent ratio is altered with respect to the reactants to control the formation of by-products.

Scheme-5

Methyl 3-aminocrotanate  3-Nitrobenzaldehyde  Acetoacetic acid 2-(N-Benzyl-N-methylamino)ethyl ester 1. Condensation
2. HCl Nicardipine Hydrochloride An example according to this invention is the synthesis of nicardipine hydrochloride from 3-nitrobenzaldehyde (about 2 mole equivalent), 3-amino-3-methyl coronate (1 mole equivalent) and acetoacetic acid 2-(N-benzyl-N-methylamino)ethyl ester (1 mole equivalent) in isopropanol (at 24 times the weight medium). This reaction yields 70% (by mole) of the desired product, and a purity greater than 99% upon recrystallisation from acetone.

Nicardipine hydrochloride exhibits two polymorphic forms, one melting at about 135° C. (herein after referred as Form B) and the other melting at about 170° C. (herein after referred as Form A). Separate procedures are known in the art to obtain these polymorphs, however there is no specific process reported in the art to convert nicardipine hydrochloride Form B to nicardipine hydrochloride Form A. A detailed novel procedure to transform nicardipine Hydrochloride Form B to nicardipine hydrochloride Form A, and vice versa, is also provided by this invention.

One specific embodiment of this invention is a process of preparing nicardipine hydrochloride comprising contacting one mole equivalent of methyl 3-aminocrotonate, one mole equivalent of acetoacetic acid 2-(N-benzyl-N-methylamino) ethyl ester, and a supramolar equivalent, preferably about 1.4 to 2.0 mole equivalent, of 3-nitrobenzaldehyde in an organic solvent medium; the solvent medium preferably is present in a weight amount of at least about 20 times the weight of any one of the reactants. (Of course, as the densities are similar, depending on the measuring equipment available, the solvent medium can be present in a volume amount of at least about 20 times the volume of any one reactant.)

In another specific embodiment, this invention provides a process of preparing nicardipine hydrochloride comprising contacting one mole equivalent of acetoacetic acid methyl ester, one mole equivalent of 3-aminocrotonic acid 2-(N-benzyl N-methylamino)ethyl ester, one mole equivalent of an amine base or salt, and a supramolar amount, preferably about 1.4 to 2.0 mole equivalent, of 3-nitrobenzaldehyde, all in an organic solvent medium of weight of at least about 20 times the weight of any one of the reactants.

In another specific embodiment, this invention provides a process of converting nicardipine hydrochloride Form B to nicardipine hydrochloride Form A by the steps of:
(a) providing nicardipine hydrochloride Form B in a solvent;
(b) drying the solution prepared in step (a) using a drying agent or by distillation;
(c) concentrating the solution (preferably to a desired minimum volume);
(d) adding another organic solvent to dilute the solution; and
(e) inducing crystallization by seeding with nicardipine hydrochloride Form A, and cooling below room temperature In a related embodiment, this invention provides a process of converting nicardipine hydrochloride Form A to nicardipine hydrochloride Form B by the steps of:
(a) providing nicardipine hydrochloride Form A in a solvent;
(b) concentrating the solution to a minimum volume;
(c) adding another organic solvent to dilute the solution; and
(d) inducing crystallization by seeding with nicardipine hydrochloride Form B, and cooling to below room temperature L-arginine has been used in the art for preparing parenteral compositions of poorly soluble drugs and pro-drugs, and as an excipient in a wide range of pharmaceutical application. L-Arginine is categorically considered to be an organic base having three pKa values: 2.18, 9.09 and 13.2. As noted in the Background section, the typical buffering activity of a substance occurs in the range of pH=pKa±1. That is, buffering capacity is maximum when pH=pKa, and is effective within the range pH=pKa±1. Accordingly, in the pH range from 3.28 to about 8.09, L-arginine is not considered to have any buffering activity. The enhanced solubility of nicardipine hydrochloride in aqueous solution in the presence of L-arginine and hydrochloric acid at a pH of about 3.5, and without the presence of a known buffer, as shown in this invention, is therefore unexpected and surprising. While not desirous of being constrained to any particular theory, the increased solubility might be due the steady state equilibrium exchange of chloride ions between nicardipine and L-arginine molecules. Such a kinetic equilibrium can be disturbed by excess addition of chloride ion or L-arginine, resulting in precipitation of nicardipine hydrochloride. According to this invention, a nicardipine solution containing an amount of L-arginine less than the amount of nicardipine hydrochloride is found to be stable.

This invention provides a novel process of preparing stable nicardipine solution using L-arginine at a ratio less than the amount of nicardipine hydrochloride present, preferably at less than 20%, more preferably less than 5%, and most preferably less than 1% by weight with respect to nicardipine hydrochloride. It is show in the experiments following that the solution containing L-arginine is not buffered (there is no buffering action against an added base) in comparison with the commercial product (Cardene brand) buffered with citric acid, and exhibits approximately the same changes in pH in comparison with an unbuffered nicardipine solution when challenged with an added base.

Thus, another specific embodiment of this invention is a process of preparing parenteral solution of nicardipine hydrochloride in aqueous medium by the steps of:
a) dissolving nicardipine hydrochloride in a aqueous medium containing less than 2.5 mg/mL of L-arginine, and hydrochloric acid, at a temperature between about 20° and about 50° C. to yield at least 2.5 mg/mL of nicardipine solution;
b) adding a quantity of sorbitol effective to adjust the isotonicity of the solution; and
c) adjusting the pH of the aqueous solution to about 3.5.

The following examples illustrate the practical application of the principles of this invention and various novel aspects thereof. As shown by in the examples, using more than one mole equivalent of the aromatic aldehyde increases the yield by more than 40% compared with yields obtained using equalmolar or submolar (less than one mole equivalent on amounts of the aldehyde. Also as shown by the examples are processes for preparing a stable parenteral solution of nicardipine hydrochloride and L-arginine at a pH greater than about 3.2, and the novel solution so prepared, and to making an isotonic solution of the same and that novel composition so made.

While the process disclosed herein is exemplified for nicardipine, in general the process is useful for making unsymmetrical 4-aryl-2,3,5,6-substituted-1,4-dihydropyridine esters, and parenteral solutions thereof. Also, improved parenteral solutions of other 1,4-dihydropyridine compounds can be made by using L-arginine and an acid at a pH between about 3.2 and 8.0 to enhance the solubility of the compound.

Example 1

Preparation of Nicardipine Hydrochloride with 2 Equivalent of Aldehyde

Into a round bottom flask fitted with a thermometer pocket, reflux condenser and a mechanical stirrer, added acetoacetic acid 2-(N-benzyl-N-methylamino)ethyl ester (100.0 g, 400 mmol), methyl 3-aminocrotonate (46.2 g, 400 mmol) and 3-nitro benzaldehyde (121.25 g, 800 mmol) and 2500 mL isopropyl alcohol. Slowly raised the temperature of the reaction mixture to about 80° C. until the completion of the reaction (monitored by HPLC). The residue obtained after evaporation of isopropanol was dissolved in 800 mL ethyl acetate. The unreacted excess aldehyde was removed by extraction of the ethyl acetate solution with aqueous sodium bisulfite solution. Further the ethyl acetate layer was treated with dilute hydrochloric acid. The aqueous layer was discarded. The ethyl acetate layer was dried with sodium sulfate and cooled to about 0 to 5° C. and stirred for about 2 hrs. The precipitate was isolated by filtration. The precipitated nicardipine hydrochloride was characterized by mass spectrometry and NMR, and dried under vacuum for 3-4 hrs at 45-50° C. to get crude nicardipine hydrochloride 140 g. melting point 134° C. (Form B).

Example 2

Preparation of Nicardipine Hydrochloride Form A

The crude nicardipine hydrochloride (140 g) prepared as in Example 1 was dissolved in 500 ml methanol and then concentrated by evaporation under vacuum into a thick mass. Acetone (500 ml) was added and the solution filtered to remove any insoluble matter. Another 500 mL acetone was added and stirred for about 8 hrs to precipitate the hydrochloride salt at about 0 to −10° C. The filtered solid was washed with chilled acetone followed by drying under vacuum at about 50° C. Melting point 170° C. (indicative of Form A): yield 130 g. The powder XRD data of this sample matched that of nicardipine hydrochloride published in International center of diffraction data (00-044-1783).

Example-3

Preparation of Nicardipine Hydrochloride Form a

Figure 2:
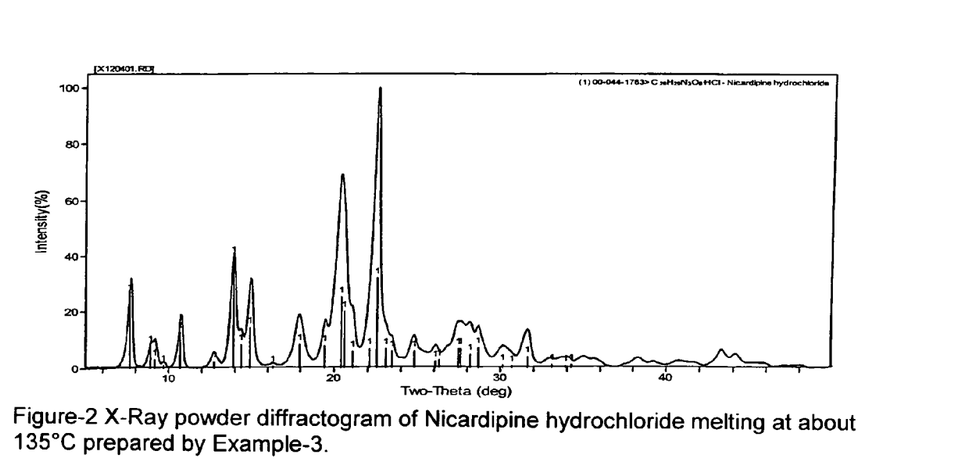
FIG. 2 is an X-Ray powder diffractogram of nicardipine hydrochloride Form A prepared according to example 3 of this invention.
Figure 3:
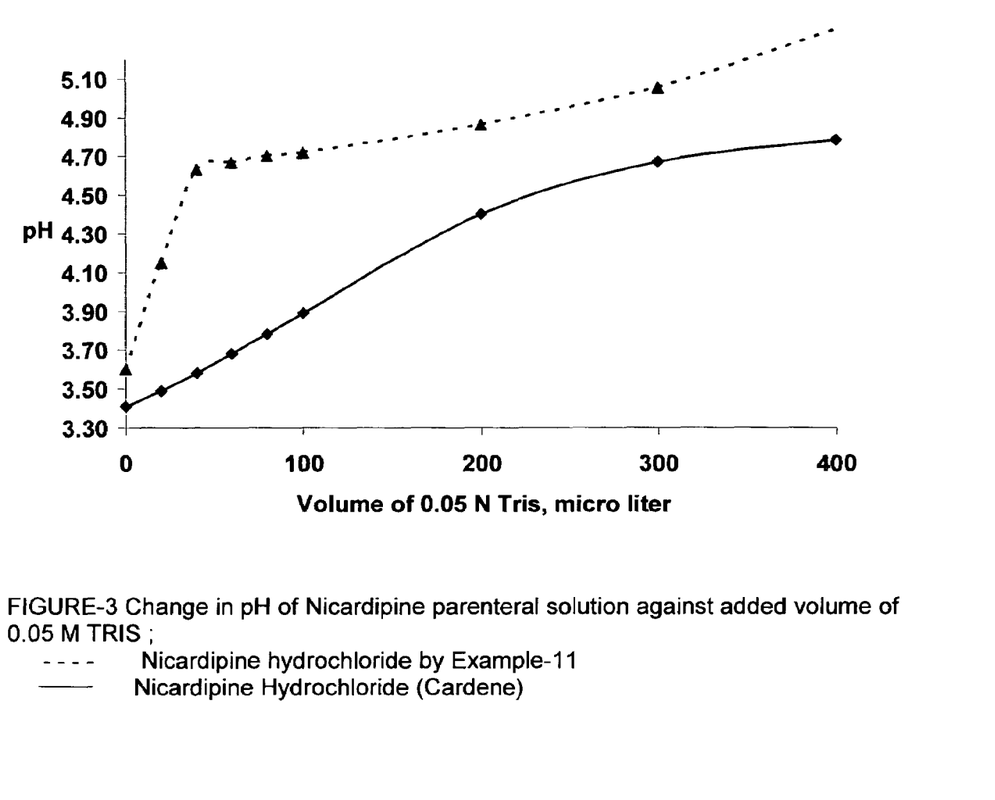
FIG. 3 is a plot of the change in pH of a nicardipine parenteral solution against an added volume of 0.05 M TRIS

The crude nicardipine hydrochloride (140 g) prepared as in Example 1 was dissolved in 500 ml methanol and then concentrated by evaporation under vacuum into a thick mass. Acetone (1000 ml) was added, and then added about 2 g of nicardipine hydrochloride Form A, and stirring slowly for about 8 hrs precipitated the hydrochloride salt at about 0 to −10° C. The filtered solid was washed with chilled acetone followed by drying under vacuum at about 50° C. Melting point 170° C. (Form A). Yield 130 g. Powder XRD data of this sample (FIG. 2) matches to that of nicardipine hydrochloride published in International center of diffraction data (00-044-1783).

Example-4

Recrystallisation of Nicardipine Hydrochloride Form B

Figure 1:
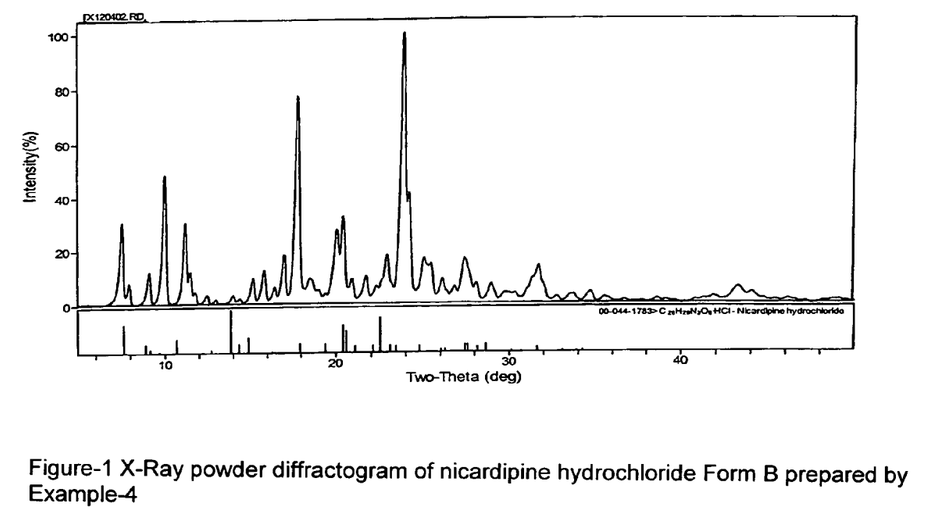
FIG. 1 is an X-Ray powder diffractogram of nicardipine hydrochloride Form B prepared according to example 4 of this invention.

The crude nicardipine hydrochloride (140 g) was dissolved in 500 ml methanol, concentrated by evaporation under vacuum, and to the thick mass, Ethyl acetate (1000 ml) was added and stirred for about 8 hrs to completely precipitate the Hydrochloride salt at about −10 to −25° C. Filtered solid was and washed with precooled acetone followed by drying under vacuum at about 50° C. Melting point 136° C. (Form B) and Yield 120 g. Powder XRD data of this sample (FIG. 1) does not match to that of nicardipine hydrochloride published in International center of diffraction data (00-044-1783).

Example-5

Conversion of Nicardipine Hydrochloride (Form B) Melting at about 135° C. to Nicardipine Hydrochloride (Form A) Melting at about 170° C.

The nicardipine hydrochloride melting at about 135° C. (140 g) prepared as in Example-4 was dissolved in 500 ml methanol, dried with sodium sulfate, concentrated by evaporation under vacuum, and to the thick mass, acetone (800 ml) was added, filtered to remove insoluble matter, and stirred for about 6 hrs to completely precipitate the hydrochloride salt at about 0° to −25° C. Filtered solid was and washed with precooled acetone followed by drying under vacuum at about 50° C. Melting point 171° C. and Yield 126 g Example-6

Preparation of Nicardipine Hydrochloride with 1 Equivalent of Aldehyde

Into a round bottom flask fitted with a thermometer pocket, reflux condenser and a mechanical stirrer, added acetoacetic acid 2-(N-benzyl-N-methylamino)ethyl ester (100 g, 400 mmol) methyl 3-aminocrotonate. (46.2 g, 400 mmol) and 3-nitro benzaldehyde (60.6 g, 400 mmol) and 2500 mL isopropyl alcohol. Slowly raise the temperature of the reaction mixture to about 80° C. until the completion of the reaction (monitored by HPLC). The residue obtained after evaporation of isopropanol was dissolved in 800 mL ethyl acetate. The unreacted excess aldehyde was removed by extraction of the ethyl acetate solution with aqueous sodium bisulfite solution. Further the ethyl acetate layer was treated with dilute Hydrochloric acid. The aqueous layer was discarded. The ethyl acetate layer was dried with sodium sulfate and cooled to about 0 to 5° C. and stirred for about 2 hrs. The precipitate was isolated by filtration. Dried the solid under vacuum for 3-4 hrs at 45-50 C to get crude hydrochloride 63 g.

Example-7

Preparation of Nicardipine Hydrochloride with 1.5 Equivalent of Aldehyde

Into a round bottom flask fitted with a thermometer pocket, reflux condenser and a mechanical stirrer, added acetoacetic acid 2-(N-benzyl-N-methylamino)ethyl ester (100.0 g, 400 mmol), methyl 3-aminocrotonate (46.2 g, 400 mmol) and 3-nitro benzaldehyde (90.9 g, 600 mmol) and 2500 mL Isopropyl alcohol. Slowly raise the temperature of the reaction mixture to about 80° C. till the completion of the reaction (monitored by HPLC). The residue obtained after evaporation of isopropanol was dissolved in 800 mL ethyl acetate. The unreacted excess aldehyde was removed by extraction of the ethyl acetate solution with aqueous sodium bisulfite solution. Further the ethyl acetate layer was treated with dilute hydrochloric acid. The aqueous layer was discarded. The ethyl acetate layer was dried with sodium sulfate and cooled to about 0 to 5° C. and stirred for about 2 hrs. The precipitate was isolated by filtration. Dried the solid under vacuum for 3-4 hrs at 45-50 C to get crude hydrochloride 115 g The results of examples 1, 6, and 7 are summarized in TABLE-1 below. "Mole ratio" is the molar ratio of 3-Nitrobenzaldehyde to acetoacetic acid 2-(N-benzyl-N-methylamino)ethyl ester. "Yield" is calculated by mole % nicardipine hydrochloride produced with respect to the starting material acetoacetic acid 2-(N-benzyl-N-methylamino)ethyl ester. Form B purity is based on crude Form B. Form A purity is based on purity after crystallization of Form A. The results show that a greater than equimolar amount of the aldehyde provides a better yield and better purity, and that yield and purity increase as the molar ratio moves from one to two.

TABLE 1

Yield of Nicardipine Hydrochloride

| Example | Mole ratio | Yield % | % Purity of Form B | % Purity of Form A |
|---|---|---|---|---|
| 6 | 1.0 | 30.4 | 97.2 | 99.5 |
| 7 | 1.5 | 55.5 | 98.5 | 99.5 |
| 1 | 2.0 | 67.6 | 98.6 | 99.5 |

Example-8

Preparation of 2-(N,N-Dimethylamino)ethyl Methyl 1,4-dihydro-2,6-dimethyl-4-(m-nitrophenyl)-3,5-pyridinedicarboxylate Into a round bottom flask fitted with a thermometer pocket, reflux condenser and a mechanical stirrer, added Acetoacetic acid 2-(N,N-Dimethylamino)ethyl ester (69.5 g, 400 mmol), Methyl 3-aminocrotonate. (46.2 g, 400 mmol) and 3-nitro benzaldehyde (121.25 g, 800 mmol) and 2500 mL Isopropyl alcohol. Slowly raise the temperature of the reaction mixture to about 80° C. till the completion of the reaction (monitored by HPLC). The residue obtained after evaporation of isopropanol was dissolved in 800 mL ethyl acetate. Further the ethyl acetate layer was treated with dilute Hydrochloric acid. The aqueous layer was discarded. The Ethyl acetate layer was dried with sodium sulfate and cooled to about 0 to 5° C. and stirred for about 2 hrs. The precipitate was isolated by filtration. Dried the solid under vacuum for 3-4 hrs at 45-50 C to get crude hydrochloride 102 g.

Example 9

Preparation of Nicardipine Hydrochloride with 1 Equivalent of Aldehyde and Reduced Solvent Volume Into a round bottom flask fitted with a thermometer pocket, reflux condenser and a mechanical stirrer, added Acetoacetic acid 2-(N-benzyl-N-methylamino)ethyl ester (100.0 g, 400 mmol), Methyl 3-aminocrotonate. (46.2 g, 400 mmol) and 3-nitro benzaldehyde (121.25 g, 800 mmol) and 1250 mL Isopropyl alcohol. Slowly raise the temperature of the reaction mixture to about 80° C. till the completion of the reaction (monitored by HPLC). The residue obtained after evaporation of isopropanol was dissolved in 800 mL ethyl acetate. The unreacted excess aldehyde was removed by extraction of the ethyl acetate solution with aqueous sodium bisulfite solution. The ethyl acetate layer was treated with dilute hydrochloric acid. The aqueous layer was discarded. The ethyl acetate layer was dried with sodium sulfate and cooled to about 0 to 5° C. and stirred for about 8 hrs. Precipitated nicardipine hydrochloride was isolated by filtration and characterized by mass spec and NMR and found to be 70% pure by chromatography. Dried solid under vacuum for 3-4 hrs at 45-50° C. yielded 90 g.

Example-10

Conversion of Nicardipine Hydrochloride (Form A) Melting at about 170° C. to Nicardipine Hydrochloride (Form B) Melting at about 135° C.

The nicardipine hydrochloride melting at about 170° C. (Form A, 100 g) was dissolved in 500 ml methanol, concentrated by evaporation under vacuum, and to the thick mass, about 1000 ml of Ethyl acetate was added and stirred for about 9 hrs to precipitate the Hydrochloride salt at about 0 to −25° C. Filtered solid was and washed with pre-cooled acetone followed by drying under vacuum at about 50° C. Melting point 136° C. (Form B, 90 g)

Example-11

Preparation of Parenteral Solution of Nicardipine Hydrochloride (2.5 mg/mL)

Into about 400 mL of water for injection added 850 mg of L-Arginine and dissolved. The pH of this solution was adjusted to about 3.6 using hydrochloric acid. Added 1.25 g of nicardipine hydrochloride under stirring at about 25-30° C. for about 30 min. Added about 24 g of D-sorbitol and dissolved. pH of the solution was adjusted with hydrochloride acid to 3.6 and compounded to 500 mL.

Example-12

Preparation of Parenteral Solution of Nicardipine Hydrochloride (2.5 mg/mL)

Into about 400 mL of water for injection added 425 mg of L-Arginine and dissolved. The pH of this solution was adjusted to about 3.6 using hydrochloric acid. Added 1.25 g of nicardipine hydrochloride under stirring at about 25-30° C. for about 30 min. Added about 24 g of D-sorbitol and dissolved. pH of the solution was adjusted with hydrochloride acid to 3.6 and compounded to 500 mL.

Example-13

Preparation of Parenteral Solution of Nicardipine Hydrochloride (2.5 mg/mL)

Into about 400 mL of water for injection added 850 mg of L-Arginine and dissolved. The pH of this solution was adjusted to about 3.6 using citric acid. Added 1.25 g of nicardipine hydrochloride under stirring at about 25-30° C. for about 30 min. Added about 24 g of D-sorbitol and dissolved. pH of the solution was adjusted with citric acid to 3.6 and compounded to 500 mL.

Example-14

Preparation of Parenteral Solution of Nicardipine Hydrochloride (2.5 mg/mL)

Into about 400 mL of water for injection added 850 mg of L-Arginine and dissolved. The pH of this solution was adjusted to about 3.6 using citric acid. Added 1.25 g of nicardipine hydrochloride under stirring at about 25-30° C. for about 30 min. Added about 24 g of D-sorbitol and dissolved. pH of the solution was adjusted with citric acid to 3.6 and compounded to 500 mL.

Example-15

Preparation of Parenteral Solution of Nicardipine Hydrochloride (2.5 mg/mL)

Into about 400 mL of water for injection added 262.5 mg citric acid monohydrate. The pH of this solution was adjusted to about 3.6 using L-arginine. Added 1.25 g of nicardipine hydrochloride under stirring at about 25-30° C. for about 30 min. Added about 24 g of D-sorbitol and dissolved. pH of the solution was adjusted with citric acid monohydrate to 3.6 and compounded to 500 mL.

Example-16

Preparation of Parenteral Solution of Nifedipine Hydrochloride (2.5 mg/mL)

Into about 400 mL of water for injection added 850 mg of L-Arginine and dissolved. The pH of this solution was adjusted to about 3.6 using citric acid. Added 1.25 g of Nifedipine hydrochloride under stirring at about 25-30° C. for about 30 min. Added about 24 g of D-sorbitol and dissolved. pH of the solution was adjusted with citric acid to 3.6 and compounded to 500 mL.

Example-17

Preparation of Parenteral Solution of Nisoldipine Hydrochloride (2.5 mg/mL)

Into about 400 mL of water for injection added 850 mg of L-Arginine and dissolved. The pH of this solution was adjusted to about 3.6 using citric acid. Added 1.25 g of Nisoldipine hydrochloride under stirring at about 25-30° C. for about 30 min. Added about 24 g of D-sorbitol and dissolved. pH of the solution was adjusted with citric acid to 3.6 and compounded to 500 mL.

Example-18

Determination of Buffer Action of Nicardipine Hydrochloride Solution by Addition of a Base

Ten point zero (10.0) mL of parenteral solution obtained as described in Example-11 was titrated against 0.05 M TRIS solution (hydroxymethyl aminomethane buffer) potentiometrically. For comparison, nicardipine hydrochloride formulated with a citric acid buffer (Cardene brand, bought commercially, sample lot no. 055038. expiry date November 2006) also was titrated against 0.05 M TRIS solution. The results are furnished in the TABLE-2

TABLE 2

Change in pH of nicardipine solution upon addition of 0.05M TRIS

| Volume of 0.05 M TRIS buffer, Micro Liter | pH of Cardene Solution, Citric acid buffer | pH of Nicardipine Hydrochloride solution obtained with Example 11, no buffer |
|---|---|---|
| 0 | 3.41 | 3.65 |
| 20 | 3.49 | 4.15 |
| 40 | 3.58 | 4.63 |
| 60 | 3.68 | 4.67 |
| 80 | 3.78 | 4.70 |
| 100 | 3.89 | 4.72 |
| 200 | 4.40 | 4.86 |
| 300 | 4.67 | 5.05 |
| 400 | 4.78 | 5.35 |

Example-19

Effect of Change in pH of a Dextrose Solution in the Range 3 to 7 pH upon Addition of Nicardipine Hydrochloride

Figure 4:
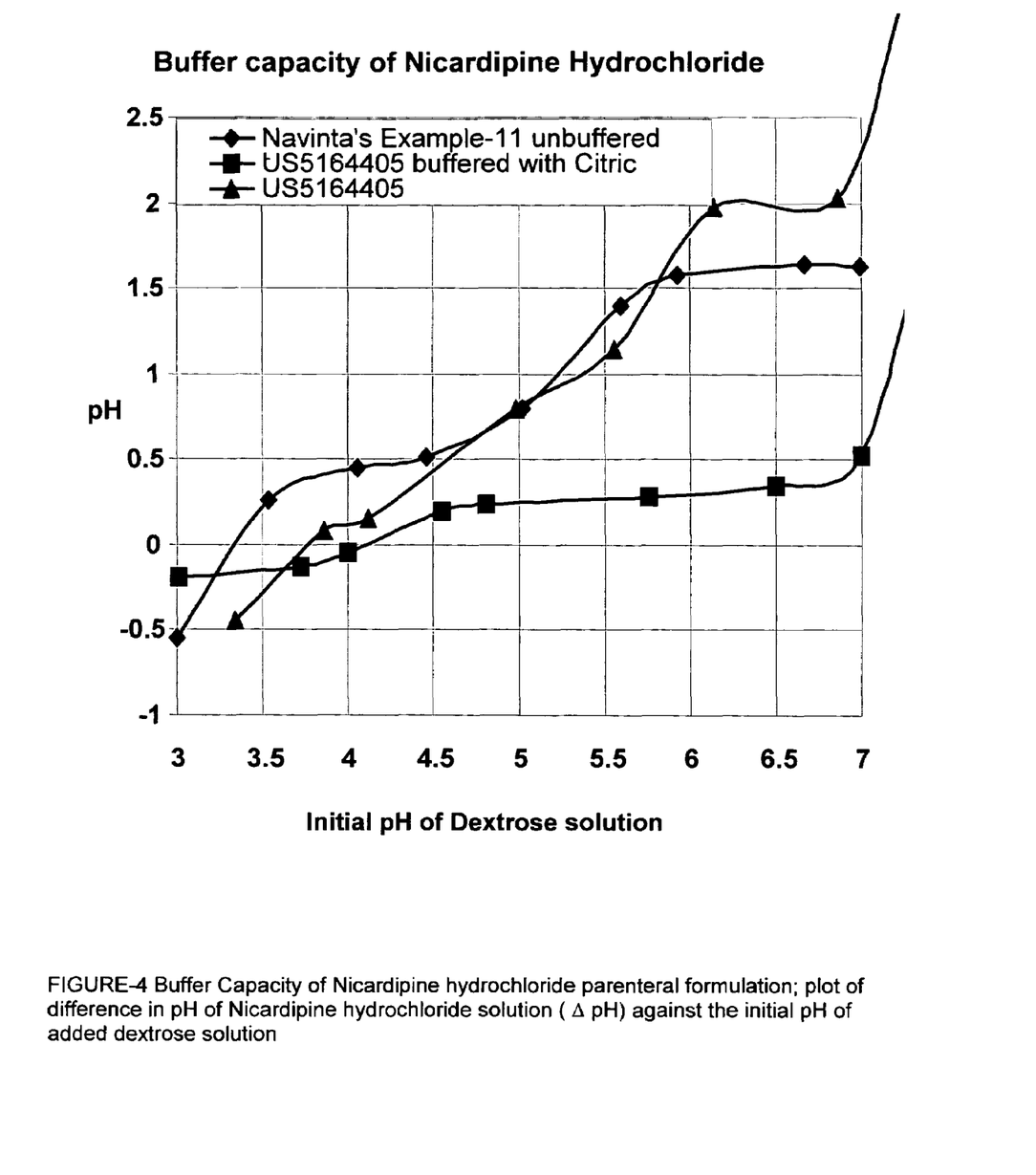
FIG. 4 depicts the change in pH value of a nicardipine hydrochloride solution against the initial pH of added dextrose solution compared with the prior art organic acid buffered solution and the prior art without the organic acid buffer.

Effect of change in pH of a dextrose solution in the range 3 to 7 pH upon the addition of nicardipine hydrochloride solution was performed by first measuring the initial pH of the individual solutions; thereafter, one (1) volume of nicardipine hydrochloride solution prepared by Example-11 was mixed with nine (9) volumes of dextrose solution and the pH adjusted to a desired value in the range 3 to 7. The pH data are furnished in Table-3; the plot of difference in the pH of nicardipine hydrochloride solution before and after dilution with 5% dextrose solution versus the initial pH of dextrose solution is shown in FIG. 4. For comparison, a similar plot for the pH data reported in U.S. Pat. No. 5,164,405 for buffered and unbufferred nicardipine solution is also provided.

TABLE 4

Change in Initial pH of dextrose solution
Initial pH of Nicardipine Hydrochloride solution for example 11 is 3.60.
Initial pH of Nicardipine Hydrochloride solution reported in U.S. Pat. No. 5,164,405 is 3.86

| Nicardipine Hydrochloride solution Prepared by the process of this invention | | | Nicardipine Hydrochloride solution Buffered reported in Table 10 US patent U.S. Pat. No. 5,164,405 | | | Nicardipine Hydrochloride solution unbufferred reported in Table 11 US patent U.S. Pat. No. 5,164,405 | | |
|---|---|---|---|---|---|---|---|---|
| Example-11 | | | Final pH of | | | Final pH of | | |
| Initial pH of Dextrose solution | Final pH of mixture of dextrose and Nicardipine solution | Δ pH | Initial pH of Dextrose solution | mixture of dextrose and Nicardipine solution | Δ pH | Initial pH of Dextrose solution | mixture of dextrose and Nicardipine solution | Δ pH |
| 3.00 | 3.05 | −0.55 | 3.01 | 3.67 | −0.19 | 3.34 | 3.42 | −0.44 |
| 3.54 | 3.86 | 0.26 | 3.72 | 3.73 | −0.13 | 3.86 | 3.94 | 0.08 |
| 4.05 | 4.05 | 0.45 | 4.00 | 3.82 | −0.04 | 4.12 | 4.02 | 0.16 |
| 4.46 | 4.11 | 0.51 | 4.55 | 4.06 | 0.20 | 4.99 | 4.66 | 0.80 |
| 5.02 | 4.40 | 0.80 | 4.81 | 4.10 | 0.24 | 5.56 | 5.00 | 1.14 |
| 5.60 | 5.00 | 1.40 | 5.76 | 4.14 | 0.28 | 6.14 | 5.83 | 1.97 |
| 5.93 | 5.17 | 1.57 | 6.50 | 4.21 | 0.35 | 6.86 | 5.89 | 2.03 |

TABLE 4-continued

Change in Initial pH of dextrose solution
Initial pH of Nicardipine Hydrochloride solution for example 11 is 3.60.
Initial pH of Nicardipine Hydrochloride solution reported in U.S. Pat. No. 5,164,405 is 3.86

| Nicardipine Hydrochloride solution Prepared by the process of this invention | | | Nicardipine Hydrochloride solution Buffered reported in Table 10 US patent U.S. Pat. No. 5,164,405 | | | Nicardipine Hydrochloride solution unbuffered reported in Table 11 US patent U.S. Pat. No. 5,164,405 | | |
|---|---|---|---|---|---|---|---|---|
| Example-11 | | | Final pH of | | | Final pH of | | |
| Initial pH of Dextrose solution | Final pH of mixture of dextrose and Nicardipine solution | Δ pH | Initial pH of Dextrose solution | mixture of dextrose and Nicardipine solution | Δ pH | Initial pH of Dextrose solution | mixture of dextrose and Nicardipine solution | Δ pH |
| 6.67 | 5.24 | 1.64 | 7.00 | 4.38 | 0.52 | 7.26 | 7.11 | 3.25 |
| 6.99 | 5.23 | 1.63 | 7.49 | 6.24 | 2.38 | | | |

Δ pH = (pH of Nicardipine injection – Final pH of mixture of Nicardipine injection and dextrose solution)

Example 20

Stability Testing

According to ICH guidelines, stability testing of the present formulation in comparison with that of the examples described in JP 11193234. The storage conditions were controlled at 40° C. and 75% relative humidity.

| | | Comparative Examples, from JP 11193234 | | | | | |
|---|---|---|---|---|---|---|---|
| | | | | | | Amount of Nicardipine HCl, mg | |
| Ex. no. | Nicardipine HCl, mg | Acid, mg | NaCl, mg | Amino acid, mg | Final pH adjustment with NaOH or HCl | Initial | 21 days at 60° C. |
| 1 | 100 | Phosphoric, 84.5 | 510 | — | — | 100 | 91.3 |
| 2 | 100 | — | 560 | L-Alanine, 900 | 3.8 | 100 | 92.7 |
| 3 | 100 | — | 685 | L-Glutamic acid, 900 | 4.0 | 100 | 93.2 |
| 4 | 100 | Citric, 80 | 520 | L-Aminoacetic acid, 900 | 3.7 | 100 | 97.7 |
| 5 | 100 | Lactic, 50 | 515 | L-Aminoacetic acid, 900 | 3.7 | 100 | 95.6 |
| 6 | 100 | Tartaric, 60 | 520 | L-Aminoacetic acid, 900 | — | 100 | 94.0 |
| Examples | | | | | | | |
| | | | | | | Purity of Nicardipine Hydrochloride, %* | |
| Example no. | Nicardipine HCl, mg/mL | Acid, mg/mL | NaCl, mg/mL | Amino acid, mg/mL | Final pH adjustment | Initial | 3 months at 40° C. |
| 20-1 | 2.5 | HCl, 0.365 | 0 | L-Arginine, 1.7 | 3.6 | 99.7 | 98.2 |

| -continued | | | | | | | |
|---|---|---|---|---|---|---|---|
| 20-2 | 2.5 | HCl, 0.183 | 0 | L-Arginine, 0.85 | 3.6 | 99.7 | 98.5 |
| 20-3 | 2.5 | Citric acid, 0.545 | 0 | L-Arginine, 0.36 | 3.6 | 99.7 | 98.4 |

*Calculated as (100—total impurities)

The final pH adjustment in the present invention, as seen in Ex. 20-1 through 20-3, does not use any sodium hydroxide as is used in the comparison. Also unlike the comparative examples, the present invention uses no sodium chloride in any of these example formulations. Still further, the weight ratio of nicardipine HCl to amino acid is never more than one and is usually much less than one (the disclosure describes from 1:1 to 1:50). In contrast, the present formulations have more active ingredient than amino acid, these examples showing a ratio of about 1.4:1.0. The present formulation thus has a low ionic strength.

The actual stability results were determined over about 90 days for the present formulations, whereas only 21 days were used for the comparative compositions. The results are not only better, but surprisingly better over a longer period of time, and show that the purity of the present formulation is initially high and remains high for three months. While not desirous of being constrained to any theory of operation, it is believed that the prior art formulation containing significant amounts of amino acid, heating to dissolve, and possibly also the presence of additional salt (NaCl) facilitates degradative reactions. Without using sodium chloride, and having less amino acid (by weight) than dihydropyridine, and perhaps also without significant use of heating to dissolve, the present formulation remains stable for a significantly longer period of time than would have been expected from the prior art formulations that appear to degrade much more rapidly.

The foregoing description is meant to be illustrative and not limiting. Various changes, modifications, and additions may become apparent to the skilled artisan upon a perusal of this specification, and such are meant to be within the scope and spirit of the invention as defined by the claims.

What is claimed is:

1. A process of manufacturing nicardipine hydrochloride comprising: providing approximately equimolar amounts of methyl-3-aminocrotonate and acetoacetic acid 2-(N-benzyl-N-methylamino)ethyl ester and reacting with at least about 1.4 mole equivalent 3-nitrobenzaldehyde in an organic solvent medium.

2. The process of claim 1, wherein the solvent medium is present in an amount of at least about 20 times the amount of any one of the reactants.

3. The process according to claim 1, wherein the solvent is one or a mixture of solvents selected from the group consisting of methanol, ethanol, isopropanol, acetone, isopropyl ether, ethyl acetate, and toluene.

4. The process according to claim 1 or 2, wherein the solvent is one or a mixture of solvents selected from the group consisting of lower alcohols, lower alkyl ketones, lower alkyl ethers, lower alkyl esters and lower alkyl benzenes.

5. A process of preparing an aqueous solution of a dihydropyridine salt, comprising: dissolving a dihydropyridine salt selected from the group consisting of nicardipine, felodipine, nifedipine, nimodipine, nisoldipine, nitrendipine, niludipine, nilvadipine, and combinations thereof in an aqueous medium at a pH of about 3.6, said medium containing L-arginine and hydrochloric acid, and at a temperature of about 25° to about 30° C.; and adding a quantity of sorbitol effective to adjust the isotonicity of the solution; and adjusting the pH with an aqueous solution of an organic base or hydrochloric acid to range from greater than 3.2 to less than about 4.0.

6. The process of claim 5, wherein the dihydropyridine salt is nicardipine hydrochloride.

7. The process of claim 5, wherein the dihydropyridine salt is nisoldipine hydrochloride.

8. The process of claim 5, wherein the dihydropyridine salt is nifedipine hydrochloride.

9. The process of claim 5, wherein the pH is adjusted to be from about 3.5 to about 3.6.

10. The process of claim 5, wherein the addition of sorbitol and adjusting the pH produce an aqueous composition suitable for parenteral administration.

11. The process of claim 1, wherein at least about 1.5 mole equivalent 3-nitrobenzaldehyde is used.

\* \* \* \* \*